(12) United States Patent
Smith et al.

(10) Patent No.: US 6,752,959 B2
(45) Date of Patent: Jun. 22, 2004

(54) HIGH-SPEED, LOW TEMPERATURE STERILIZATION AND SANITIZATION APPARATUS AND METHOD

(75) Inventors: Richard T. Smith, Ridgefield, CT (US); Parker C. Reist, Chapel Hill, NC (US); Stephen Glahn, Burlington, NC (US)

(73) Assignee: PepsiCo, Inc., Purchase, NY (US)

( * ) Notice: Subject to any disclaimer, the term of this patent is extended or adjusted under 35 U.S.C. 154(b) by 0 days.

(21) Appl. No.: 09/970,913

(22) Filed: Oct. 5, 2001

(65) Prior Publication Data

US 2003/0068251 A1 Apr. 10, 2003

(51) Int. Cl.[7] ............................. A61L 2/20; A61L 2/24
(52) U.S. Cl. ........................... 422/28; 422/1; 422/298; 422/302; 422/303; 141/89; 141/91; 53/425
(58) Field of Search .................... 422/1, 26, 28, 422/298, 302, 303, 305; 141/129, 89, 91; 53/425

(56) References Cited

U.S. PATENT DOCUMENTS

| | | | |
|---|---|---|---|
| 2,824,344 A | 2/1958 | Abrams | 21/80 |
| 3,097,658 A | 7/1963 | Runco | 134/81 |
| 3,486,295 A | 12/1969 | Rausing et al. | 53/89 |
| 3,531,908 A | 10/1970 | Rausing et al. | 53/37 |
| 3,566,575 A | 3/1971 | Lisiecki | 53/37 |
| 3,620,265 A | 11/1971 | Strople et al. | 141/81 |
| 3,694,997 A | 10/1972 | Christine et al. | 53/112 R |
| 3,791,424 A | 2/1974 | Strople et al. | 141/92 |
| 3,929,409 A | 12/1975 | Buchner et al. | 21/91 |
| 4,169,123 A | 9/1979 | Moore et al. | 422/29 |
| 4,230,663 A | 10/1980 | Forstom et al. | 422/33 |
| 4,341,329 A | 7/1982 | Kuemmerer et al. | 222/275 |
| 4,424,189 A | 1/1984 | Hick | 422/27 |
| 4,472,924 A | 9/1984 | Vögele et al. | 53/511 |
| 4,512,951 A | 4/1985 | Koubek | 422/33 |
| 4,595,560 A | 6/1986 | Buchner et al. | 422/26 |
| 4,680,163 A | 7/1987 | Blidschun et al. | 422/28 |
| 4,734,268 A | 3/1988 | Redding et al. | 422/292 |
| 4,742,667 A | 5/1988 | Müller et al. | 53/167 |
| 4,896,478 A | 1/1990 | Reiter | 53/426 |
| 5,007,232 A | 4/1991 | Caudill | 53/426 |
| 5,068,087 A | 11/1991 | Childers | 422/26 |
| 5,114,670 A | 5/1992 | Duffey | 422/24 |
| 5,183,644 A | 2/1993 | Martensson et al. | 422/304 |
| 5,258,162 A | 11/1993 | Andersson et al. | 422/28 |
| 5,335,479 A | 8/1994 | Lemke et al. | 53/426 |
| 5,368,828 A | 11/1994 | Carlson | 422/300 |
| 5,879,648 A | 3/1999 | Hada et al. | 422/304 |
| 5,997,827 A | 12/1999 | Mezger et al. | 422/292 |
| 6,120,730 A * | 9/2000 | Palaniappan et al. | 422/28 |
| 6,209,591 B1 * | 4/2001 | Taggart | 141/89 |
| 2002/0159915 A1 * | 10/2002 | Zelina et al. | 422/3 |

OTHER PUBLICATIONS

Merriam Webster Online Dictionary, definition of "vapor", www.webster.com.*

* cited by examiner

Primary Examiner—Robert J. Warden, Sr.
Assistant Examiner—Sean E. Conley
(74) Attorney, Agent, or Firm—Fitzpatrick, Cella, Harper & Scinto

(57) ABSTRACT

The present invention relates to a method of sterilizing and/or sanitizing a container using a sterilant vapor such as hydrogen peroxide. The sterilant vapor is discharged through a nozzle positioned in an opening of the container and the container is then purged of the discharged sterilant using a heated gas such as sterile air. The nozzle is preferably positioned no closer than 15 mm from the bottom surface or any internal surface of the container and within ⅙ to ⅚ of the height of the container. The nozzle has a diameter no greater than one-half of the diameter of the opening of the container. When containers made of non-heat set PET are used, the temperatures of the sterilant vapor and the purge gas are preferably no greater than 160° F.

71 Claims, 6 Drawing Sheets

HIGH-SPEED, LOW TEMPERATURE STERILIZATION AND SANITIZATION APPARATUS AND METHOD

FIELD OF THE INVENTION

The present invention relates to a sterilization and/or sanitization process and apparatus for containers used for aseptic packaging of products or ingredients sensitive to microbiological spoilage or contamination. The present invention is particularly useful in sterilizing or sanitizing polyethylene terephthalate (PET) containers, especially those with openings of a relatively small cross-sectional area compared to total internal surface area and those formed of non-heat set PET.

BACKGROUND OF THE INVENTION

For the purposes of this disclosure, sterilization is defined as a 6 log reduction of spores of the bacteria *Bacillus subtillis* var. *globigii*, whereas sanitization is defined as a 5 log reduction of organisms that cause spoilage of high acid products (i.e., a pH of 4.6 or less), as typified by ascospores of the yeast *Saccharomyces cerevisiae*. Sanitization can be utilized for containers that are designed or used to store high acid products (e.g., juices, juice beverages, acidified products), whereas sterilization is preferably utilized for containers that are used to store low acid products (e.g., tea, coffee, dairy products, nutraceuticals, pharmaceuticals).

Various apparatuses and methods for sterilizing or sanitizing containers are known. The known apparatuses and methods often use a sterilant such as hydrogen peroxide ($H_2O_2$) vapor. After the hydrogen peroxide vapor is discharged into the container at a relatively high temperature, the residual sterilant is then purged from the container with a hot air flush at high temperatures.

However, these known apparatuses and methods are not suitable for containers made of certain materials, such as PET and, more particularly, non-heat set PET. For example, it is difficult to eliminate residual sterilant, such as hydrogen peroxide, not only from the surface of the PET container, but also from its polymer matrix. Upon dosing of hydrogen peroxide into a non-heat set PET container, some peroxide becomes trapped in the polymer matrix and is not readily removed with the hot air flush. Although this can be quite stable for several minutes to hours, when a fluid product is introduced into the container, the hydrogen peroxide moves from the polymer matrix into the body of the fluid product, potentially compromising federal regulations for limits on peroxide residuals.

In addition, because of the relatively low vapor pressure of hydrogen peroxide at temperatures below 250° F., most existing sterilization processes depend on the use of a flush using large volumes of a gas that has been heated to a temperature well above 250° F. Because non-heat set PET possesses a glass transition temperature of 163.4° F., it is not possible to expose such containers to temperatures much above 163° F. without risk that the containers will deform. Furthermore, the size of the opening (finish) in many containers prohibits the flow of measurably large volumes of air into and out of the containers within the short period of time required for high-speed operation.

SUMMARY OF THE INVENTION

The present invention provides an apparatus and method that can sterilize or sanitize a variety of containers in a fast, economical way.

The present invention further provides an apparatus that can sterilize or sanitize containers on a mass scale, yet occupies a relatively small area.

The present invention can effectively sterilize or sanitize PET containers without deforming the containers.

The present invention can also sterilize or sanitize PET containers leaving an amount of residual sterilant that does not exceed 0.5 mg/l in a container filled with water immediately after treatment. This value is equal to or less than the limits for sterilant residual dictated by the U.S. Food and Drug Administration (FDA).

The present invention provides a sterilization and sanitization method and apparatus for rapidly and relatively inexpensively sterilizing or sanitizing any type of standard container used for packaging of pharmaceuticals, nutraceuticals, health enhancing products as well as traditional high and low acid foods.

According to one aspect of the present invention, a method of sterilizing and/or sanitizing a container includes the steps of generating a sterilant vapor and positioning a nozzle through an opening in the container and no closer than 15 mm from any internal surface of the container that is perpendicular to a principal direction of flow of sterilant vapor through the nozzle. The method further includes the steps of discharging the generated sterilant vapor through the nozzle and into the container and purging the container of the discharged sterilant.

According to another aspect of the present invention, a method of sterilizing and/or sanitizing a container, the container having an opening of a predetermined diameter, with a ratio of the interior surface area of the container to the cross-sectional area of the opening being at least 7.5, includes the steps of generating a sterilant vapor and positioning a nozzle through the opening in the container, the nozzle having a diameter no greater than one-half the predetermined diameter of the opening of the container. The method further includes the steps of discharging the generated sterilant vapor through the nozzle and into the container and purging the container of the discharged sterilant.

According to yet another aspect of the present invention, a method of sterilizing and/or sanitizing a PET container includes the steps of generating a sterilant vapor having a temperature no greater than 160° F. and positioning a nozzle through an opening in the container. The method further includes the steps of discharging the generated sterilant vapor through the nozzle and into the container and purging the container of the discharged sterilant with a heated gas having a temperature no greater than 160° F., wherein the purging step is completed no longer than 30 seconds from a beginning of the discharging step.

According to still another aspect of the present invention, an apparatus for sterilizing and/or sanitizing a container includes a generator of sterilant vapor, a nozzle communicating with the generator and a positioning mechanism for positioning the nozzle through an opening in the container and to a position no closer than 15 mm from any internal surface of the container that is perpendicular to the principal direction of flow of the sterilant vapor. The apparatus further includes a controller for controlling discharging of the generated sterilant vapor through the nozzle and into the container and purging the container of the discharged sterilant.

According to still yet another aspect of the present invention, an apparatus for sterilizing and/or sanitizing a container, the container having an opening of a predetermined diameter, with a ratio of the interior surface area of the container to the cross-sectional area of the opening being at least 7.5, includes a generator of sterilant vapor and a nozzle communicating with the generator, the nozzle having a diameter no greater than one-half the predetermined diameter of the opening of the container. The apparatus further includes a positioning mechanism for positioning the nozzle through the opening in the container and a controller for controlling discharging of the generated sterilant vapor through the nozzle and into the container and purging of the container of the discharged sterilant.

According to another aspect of the present invention, an apparatus for sterilizing and/or sanitizing a PET container includes a generator of sterilant vapor having a temperature no greater than 160° F., a nozzle communicating with the generator and a positioning mechanism for positioning the nozzle through an opening in the container. The apparatus further includes a controller for controlling discharging of the generated sterilant vapor through the nozzle and into the container and purging of the container of the discharged sterilant with a heated gas having a temperature no greater than 160° F. The controller controls purging to be completed no longer than 30 seconds from discharging of the sterilant.

According to yet another aspect of the present invention, a method of sterilizing and/or sanitizing a container includes the steps of generating a sterilant vapor, discharging the generated sterilant vapor into the container and purging the container of the discharged sterilant with heated gas. Reduction of Bacillus spores in the container by a predetermined amount X (log) is effected by satisfying the following equation:

$$X=(0.138 \times a/b)+(0.066 \times T_1)-(0.00083 \times c/b)+(0.021 \times T_2)+(0.008347 \times d)-11.357,$$

wherein
  a is the mass of discharged sterilant vapor (mg),
  b is the container volume (1),
  c is the volume of purging gas (1),
  d is the ambient relative humidity (% RH),
  $T_1$ is the temperature of the discharged sterilant vapor (° F.), and
  $T_2$ is the temperature of the purging gas (° F.).

According to yet another aspect of the present invention, a method of sterilizing and/or sanitizing a container includes the steps of generating a sterilant vapor and discharging the generated sterilant vapor into the container. The method further includes the step of purging the container of the discharged sterilant with heated gas, wherein reduction of yeast ascospores in the container by a predetermined amount Y (log) is effected by satisfying the following equation:

$$Y=(0.063 \times a/b)+(0.023 \times T_1)-(0.00036 \times c/b)+(0.052 \times T_2)+(0.009 \times d)-3.611,$$

wherein
  a is the mass of discharged sterilant vapor (mg),
  b is the container volume (1),
  c is the volume of purging gas (1),
  d is the ambient relative humidity (% RH),
  $T_1$ is the temperature of the discharged sterilant vapor (° F.), and
  $T_2$ is the temperature of the purging gas (° F.).

According to still another aspect of the present invention, a method of sterilizing and/or sanitizing a container includes the steps of generating a sterilant vapor, discharging the generated sterilant vapor into the container and purging the container of the discharged sterilant with heated gas. Reduction of the sterilant in the container to a predetermined amount Z (mg/l) is effected by satisfying the following equation:

$$Z=(0.030 \times a/b)-(0.043 \times T_1)-(0.040 \times c/b)-(0.075 \times T_2)+15.747,$$

wherein
  a is the mass of discharged sterilant vapor (mg),
  b is the container volume (1),
  c is the volume of purging gas (1),
  $T_1$ is the temperature of the discharged sterilant vapor (° F.), and
  $T_2$ is the temperature of the purging gas (° F.).

DETAILED DESCRIPTION OF THE PREFERRED EMBODIMENTS

Figure 1:
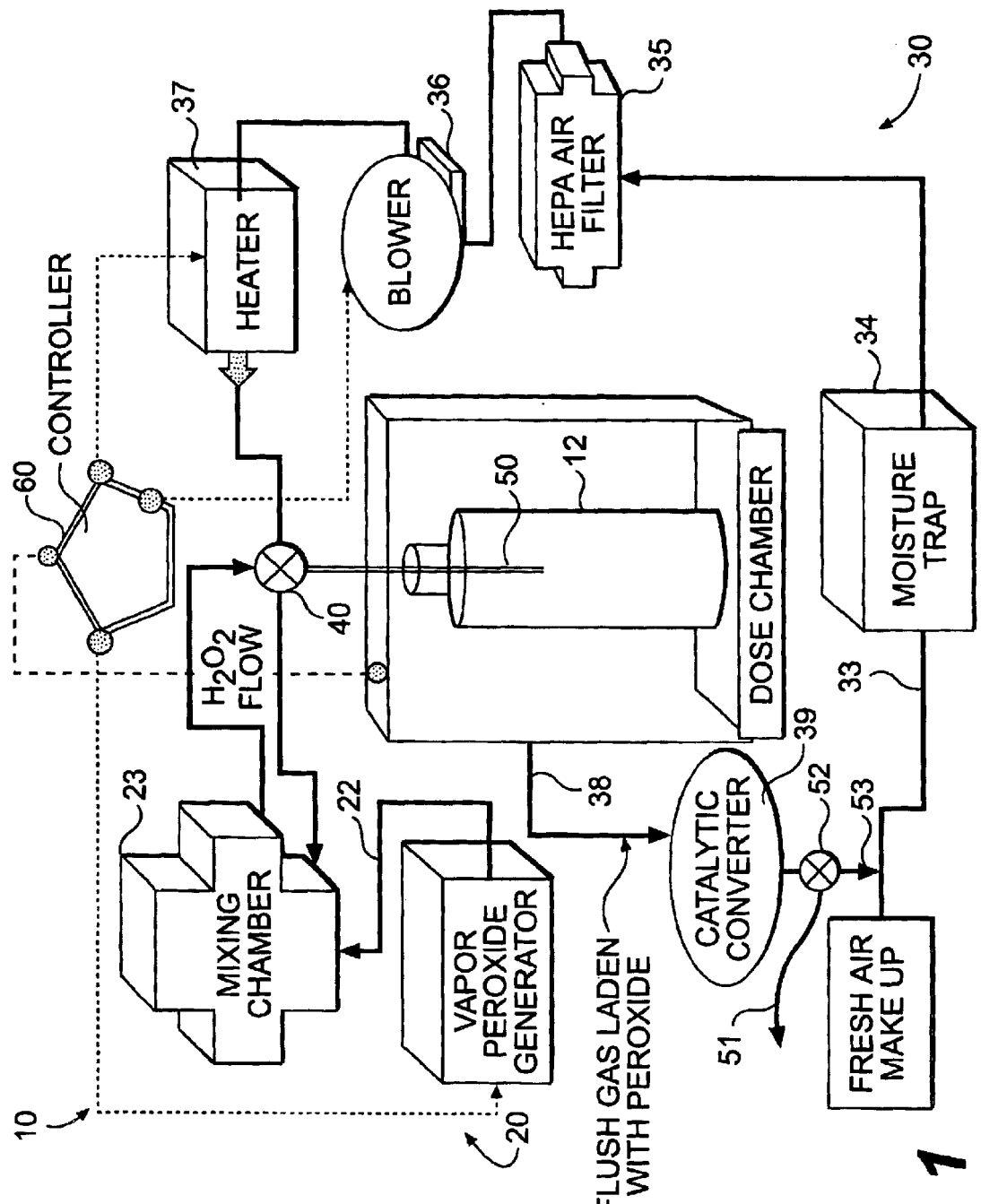
FIG. 1 is a schematic view of the overall sterilization/sanitization system according to the present invention.

A schematic view of the sterilization/sanitization system 10 of the present invention is shown in FIG. 1. System 10 includes a sterilant supply section 20 and a flush gas supply section 30. System 10 can sequentially supply sterilant from sterilant supply section 20 and flush gas from flush gas supply section 30 to container 12 by way of delivery valve 40. In order to contain the sterilant within the system, the discharging and flushing or purging steps can be performed within dose chamber or enclosure 14.

Sterilant supply section 20 preferably utilizes hydrogen peroxide, and more preferably 35% hydrogen peroxide, as the sterilant. A vapor generator 22 generates the hydrogen peroxide vapor in any known manner. The hydrogen peroxide vapor is immediately passed into a heated, moisture-free air stream. The peroxide and air mixture is passed through an insulated and heated mixing chamber 23 that contains baffles in order to obtain a uniform or homogenous mixture of peroxide in air. Unshown sensors are provided to monitor the temperature, air flow rates and peroxide concentration. The sensors feed back to a system controller 60, which can correct any deviations in the temperature, air flow rates and peroxide concentration to ensure the peroxide vapor state is maintained. The hydrogen peroxide vapor flows through sterilant supply passage 24 to delivery valve 40. When valve 40 is not actuated for delivery, it recirculates peroxide-laden air back to mixing chamber 23 through sterilant return passage 26.

Sensors are also provided in dose chamber 14 to detect the temperature and humidity therein. These conditions are monitored by controller 60 in order to control the ambient temperature and humidity during treatment. Should the chamber temperature exceed 165° F. or should the chamber humidity exceed 75%, a controller 60 prevents start of the sterilization cycle. Delivery valve 40 can be opened to continuously deliver ambient air until the chamber temperature and humidity stabilize.

Flush gas supply section 30 can provide ambient air or a pure gas such as nitrogen. When air is used to flush containers, it may be drawn into the system from the immediate environment 32. The air passes through air passage 33, through a moisture trap 34 and then through a HEPA air filter 35. The air is drawn by blower 36, which directs its discharge to heater 37. The heated air is then supplied to delivery valve 40. Air delivered to the dose chamber, whether used to condition the chamber or to flush containers, is removed from the dose chamber through return passage 38. Air enters passage 38 as a consequence of either a slight over pressure from air delivered through valve 40, a negative pressure generated through the action of blower 36 or a vacuum along passage 51, or some combination of both of these actions as balanced by manual operation of valve 52. Peroxide carried by the flush air from dose chamber into passage 38 is converted to water vapor and oxygen by action of a catalytic converter 39. Air that is free of peroxide exits the catalytic converter and can either be re-circulated if it is directed by valve 52 into passage 33 by way of passage 53 or it can be eliminated from the system through passage 51. Alternatively, valve 52 can be positioned to bleed air in various proportions to both passages 51 and 53. Thus, sterile, dry, heated air can be delivered in order to flush the sterilant.

Figure 3:
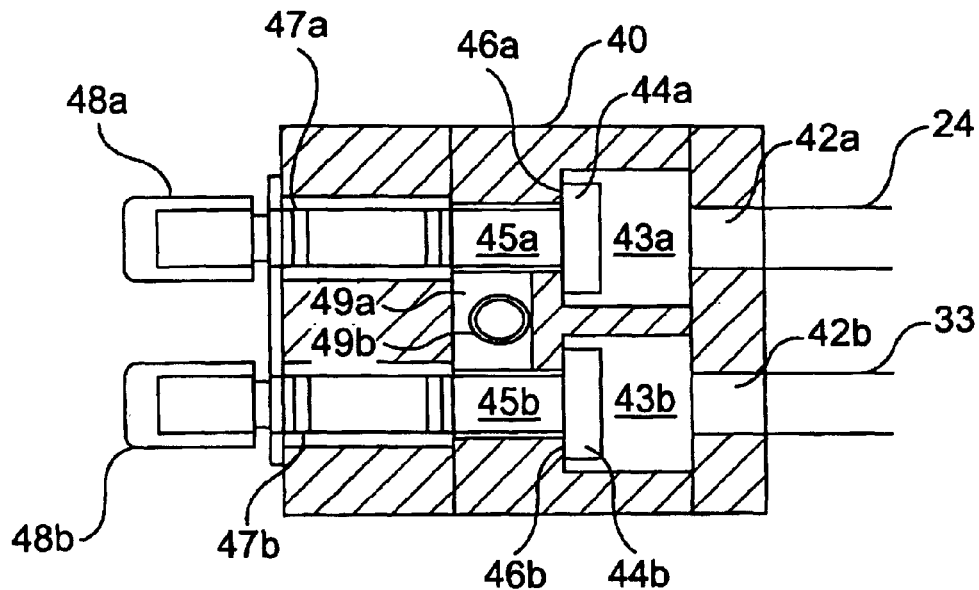
FIG. 3 is a cross-sectional plan view of the delivery valve shown in FIG. 2.
Figure 2:
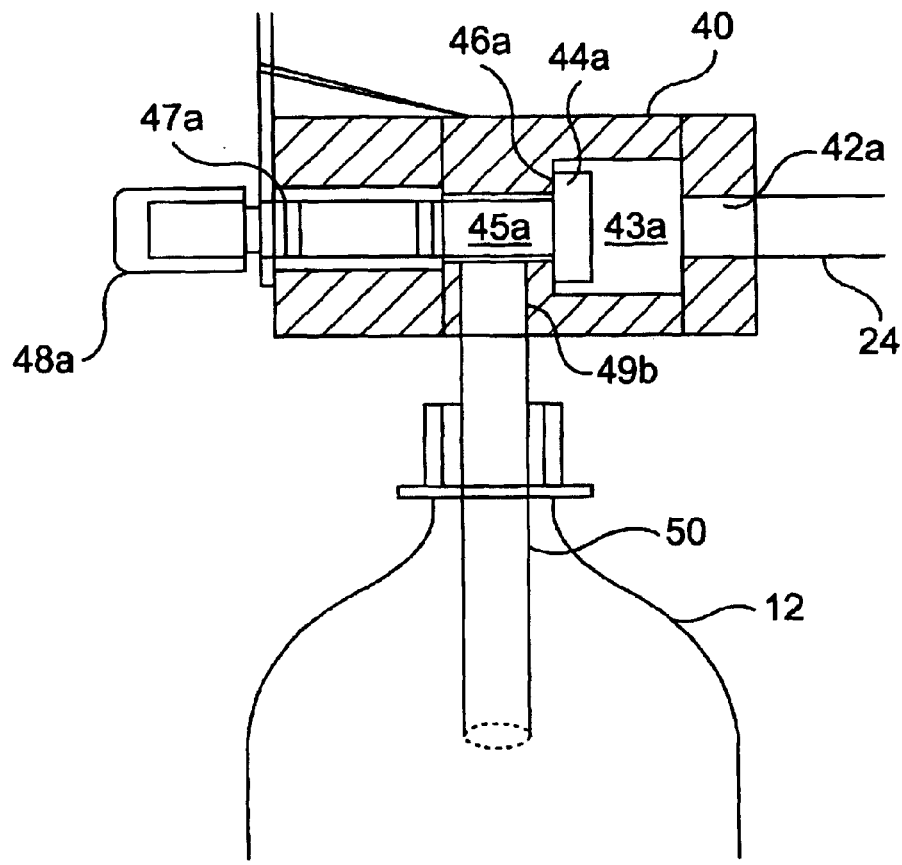
FIG. 2 is a cross-sectional side view of the delivery valve used in the sterilization/sanitization system of the present invention.

Delivery valve 40 and delivery nozzle 50 are shown in more detail in FIGS. 2 and 3. Delivery valve 40 includes inlet ports 42a and 42b for connecting with sterilant passage 24 and flush air passage 33, respectively. Not shown are connections to sterilant return passage 26. Each inlet port is connected to a respective valve chamber 43a, 43b in which a valve 44a, 44b resides. Each valve 44a, 44b is connected to a valve stem 45a, 45b movable by a respective solenoid 48a, 48b. Each valve is normally closed against respective valve seats 46a, 46b by the bias of springs 47a, 47b. When a particular valve is lifted off its respective valve seat, the respective valve chamber 43a, 43b can communicate with discharge passage 49a which includes a discharge port 49b. Delivery nozzle 50 is connected to discharge port 49d. Each solenoid 48a, 48b is independently actuable to lift valves 44a, 44b off valve seats 46a, 46b to selectively allow sterilant vapor from passage 24 or flush air from passage 33 to flow through the valve passage and discharge passage into delivery nozzle 50. Delivery valve 40 is heated so as to eliminate the potential of the sterilant vapor from cooling and condensing before reaching the container surface.

In operation, the container to be sanitized or sterilized is positioned in dose chamber 14 and nozzle 50 is inserted into an opening of the container. Delivery valve 40 is then actuated to deliver a dose of sterilant vapor through nozzle 50 into the container. After a predetermined wait period, delivery valve 40 is actuated once more to deliver a supply of flush gas through nozzle 50 to evacuate the residual sterilant.

The present invention can be used for sanitizing or sterilizing internal and external surfaces of containers, which is necessary to permit aseptic packaging of products. The containers may be formed of glass, paperboard, plastic or composites thereof. The invention is especially useful in sterilizing or sanitizing a blow-molded PET container having a bottle finish or opening that is small relative to the total volume or maximum diameter of the container. Containers having an opening with a diameter no more than one-half the maximum diameter of the container meet this definition. If the ratio of the interior surface area of the closed container to the cross-sectional area of the opening equals or exceeds 7.5, the container also meets the definition. The process is particularly useful for low cost, non-heat set PET containers. In addition, the process is particularly adaptable to rapid sterilization or sanitization of containers or packages that have non-uniform surface designs, such as rippled or ribbed surfaces, embossed surfaces, pistol grip handles, center divides or enclosed pockets.

Throughout the specification and claims, the dimensions of the containers used in the present invention are given as diameters. However, the invention is not limited to use with containers of circular cross-section. Rather, the present invention can be used with containers of any shape. Accordingly, the term "diameter" used throughout the specification and claims can read on any corresponding dimension of a non-circular container.

The parameters necessary for effective sterilization or sanitization of the containers vary depending upon the container dimensions and material. For example, to sanitize a two-liter PET container for storing high acid product would require a sanitization time of 14–19 seconds, at a hydrogen peroxide vapor concentration of about 60 mg/l and flow rate of about 2 cfm at about 125° F., whereas a 0.30 liter container would require a sanitization time of 4–5 seconds. On the other hand, sterilization of a two-liter container for storing a low acid product would require a sterilization time of 24–33 seconds, while the 0.30 liter container would require 5–7 seconds. Herein, sterilization time is defined as a period beginning from the start of relative motion between a container and the nozzle toward one another and ending when the relative motion positions the container where its opening is clear of the nozzle tip and includes sterilant dose time, hold time and flush time.

Based on exhaustive experimentation, it was determined that the parameters for sterilization and sanitization can be based on mathematical models. In each of the tests, spores of the bacteria *Bacillus subtillis* var. *globigii* or ascospores of *Saccharomyces cerevisiae* were applied to the surfaces of PET containers, dried overnight and then treated with hydrogen peroxide vapor according to the system shown in FIG. 1. The peroxide was removed by flush air to a quantity of sterilant equal to or below the FDA defined limit for sterilant residual concentration. The surviving spores were immediately recovered in a large volume neutralizing buffer and plated on appropriate recovery medium.

During the course of experimentation, 1,360 data points were collected in an analysis of yeast ascospore kill by peroxide vapor, 2,320 data points were collected in the analysis of kill of Bacillus spores by peroxide vapor, and 6,834 data points were collected in the analysis of peroxide residual. The data collected during experimentation included the temperature of the heater, the temperature of the delivery valve 40 during dosing and air flush, the temperature of the nozzle 50 during dosing and flushing, the temperature of the air flush exiting the nozzle, the temperature of the peroxide exiting the nozzle, the chamber 14 humidity, the chamber peroxide concentration, the concentration of peroxide at the exterior of the chamber, the differential pressure across the delivery nozzle 50, the residual peroxide, and the surviving population of spores relative to initial concentration. The data were collected and tabulated to permit regression analysis.

Regression analysis was performed to establish relationships between observed log reduction of Bacillus spores (or yeast ascospores) as a function of log reduction peroxide dose and air flush parameters and the elimination of peroxide residual as a function of peroxide dose and air flush parameters. The regression analysis indicated that the death of microorganisms was a log linear function and the removal of peroxide residual was a linear function within the range of test parameters.

The determined relationships are as follows:

(1) Log reduction of Bacillus spores (X):

$$X=(0.138 \times a/b)+(0.066 \times T_1)-(0.00083 \times c/b)+(0.021 \times T_2)+(0.008347 \times d)-11.357$$

(2) Log reduction of yeast ascospores (Y):

$$Y=(0.063 \times a/b)+(0.023 \times T_1)-(0.00036 \times c/b)+(0.052 \times T_2)+(0.009 \times d)+3.611$$

(3) Hydrogen Peroxide residual (after 24 hours) (mg/l):

$$(Z): Z=(0.030 \times a/b)-(0.043 \times T_1)-(0.040 \times c/b)-(0.075 \times T_2)+15.747,$$

wherein
a is the mass of hydrogen peroxide per dose (mg),
b is the container volume (l),
c is the volume of flush air (l),
d is the relative humidity within the chamber 14 (% RH),
$T_1$ is the temperature of the hydrogen peroxide vapor (° F.), and
$T_2$ is the temperature of the flush air (° F.).

Figure 4:
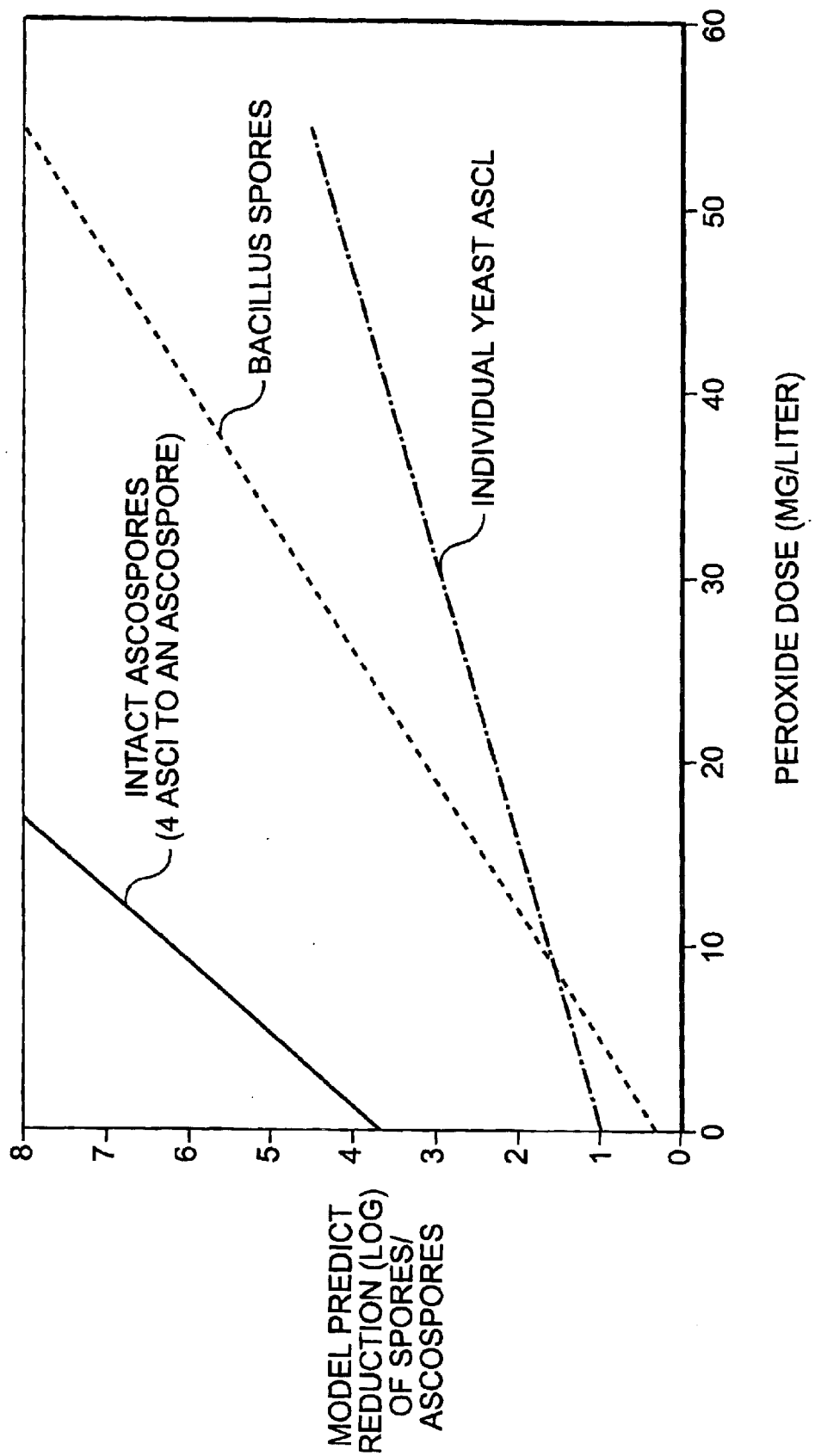
FIG. 4 is a graph showing a relationship between the reduction of contaminants and sterilant dosage.

FIG. 4 is a graph that demonstrates the impact of varying hydrogen peroxide doses and the calculated elimination of surface adhering bacterial spores and yeast ascospores.

Figure 5:
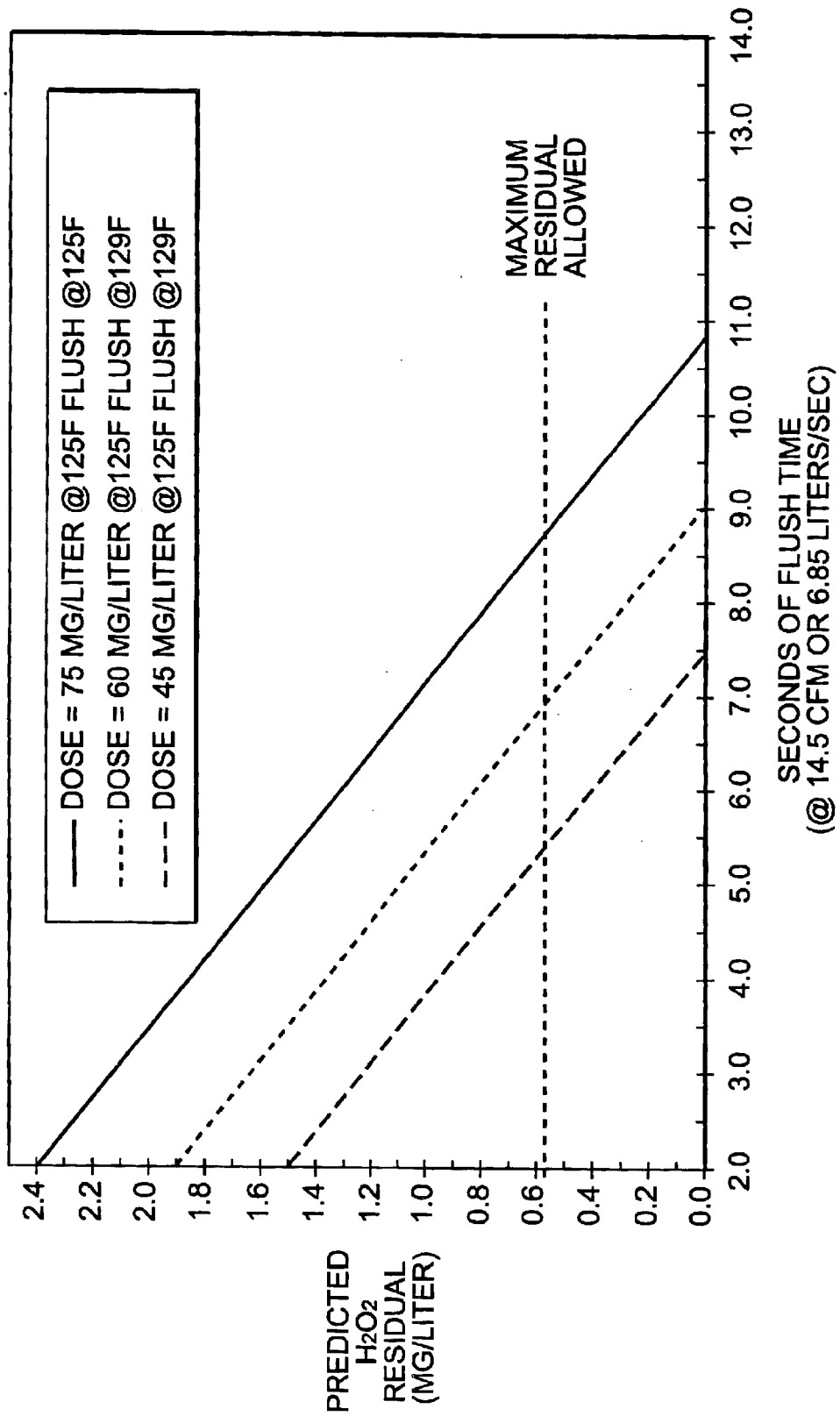
FIG. 5 is a graph showing a relationship between residual sterilant and flush time.

FIG. 5 shows the relationship of residual hydrogen peroxide versus air flush time. The dosages of hydrogen peroxide and the temperatures of the hydrogen peroxide vapor and the flush temperature were varied. The flow of the flush air was 14.5 cfm (6.85 l/s). Based on the mathematical relationships discussed above, solutions can be generated for any range of parameters. That is, for a bottle of known volume or surface area, in order to achieve the desired 6 log Bacillus reduction for sterilization or 5 log ascospore reduction for sanitization, the hydrogen peroxide dosage, flush air volume, relative humidity and temperatures of the peroxide and flush air can be determined.

It has been further discovered that the sterilization of exterior surface areas of the container that comprise the finish (opening) and shoulder of the container is critical to ensuring that the sterility of the container is maintained following treatment. To this end, delivery of the sterilant through nozzle 50 is preferably initiated before the nozzle is inserted into the container in order to permit the upper portion of the container exterior to become bathed in sterilant almost simultaneously with initiation of sterilization of the container interior.

In addition, it has been discovered that after nozzle 50 has been inserted into the container, the extent of the insertion of the nozzle impacts performance. The sterilization process optimization depends on proper positioning of the dose nozzle. For PET and plastic containers it is particularly effective when the tip of the nozzle is inserted through the opening of the container to a depth of between ⅙ and ⅝ the height of the container while sterilant is dosed. Container height is defined as the maximum column height between the top of the container finish and the lowest point of contact between filled product and the base of the container. Within this range, hydrogen peroxide delivery and removal of residual peroxide was found to be superior when compared to other positions relative to the container height. For containers having shoulders, it has been discovered that it is most effective to insert nozzle 50 through the opening of the container to just below the shoulder of the container. Further, it is critical that the tip of the nozzle be at least 15 millimeters from those surfaces of the container that are perpendicular to the principal direction of flow of peroxide from the nozzle. If the nozzle is any closer, vaporized sterilant can be released directly onto the container and create problems with residual peroxide.

The size of nozzle 50 is also a critical feature of the invention. The delivery of sterilant and removal of residual sterilant are best promoted with a delivery nozzle 50 that has a diameter no greater than one-half the diameter of the opening of the container. For example, for a container with a 28 millimeter diameter finish, the nozzle diameter should be no more than 14 millimeters. A nozzle so designed maximizes the gas exchange from the sterilization system to the container and from the container to atmosphere.

In order to allow the sterilant sufficient time to act on the contaminants, yet prevent the sterilant from being absorbed by the material of the container, the period between sterilant discharge and purging is controlled. For a 2-liter non-heat set PET container with a 28 mm finish, the complete sterilization cycle period is 30 seconds. Sterilization of smaller containers or containers with larger diameter finishes can be effected in shorter periods of time. In addition, in order to prevent damage to the PET, the temperature of the sterilant vapor and the temperature of the purge air should be no more than 160° F., which is less than the 163° F. glass transition temperature of non-heat set PET.

Figure 6:
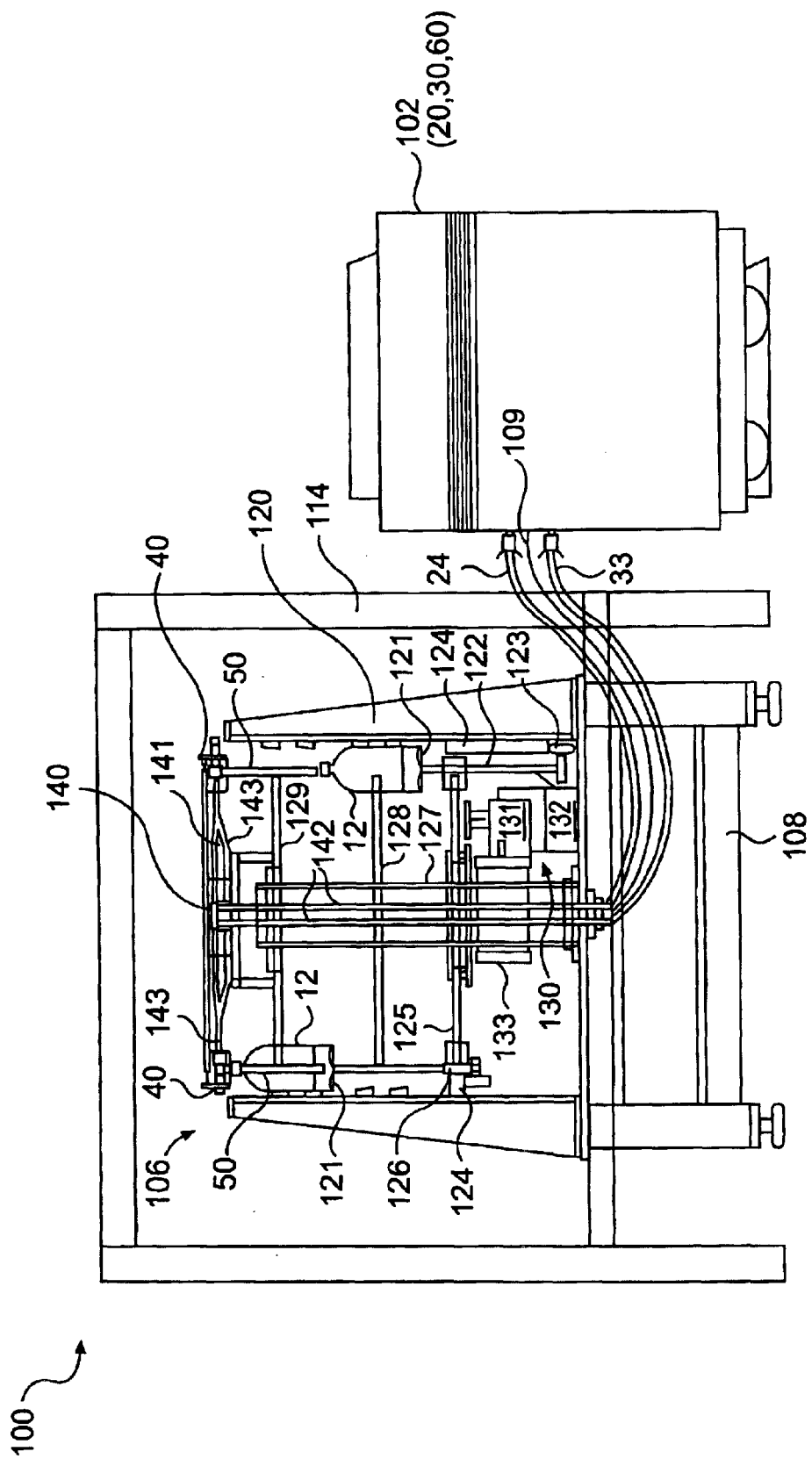
FIG. 6 is an elevational view of the sterilization/sanitization apparatus according to the present invention.
Figure 7:
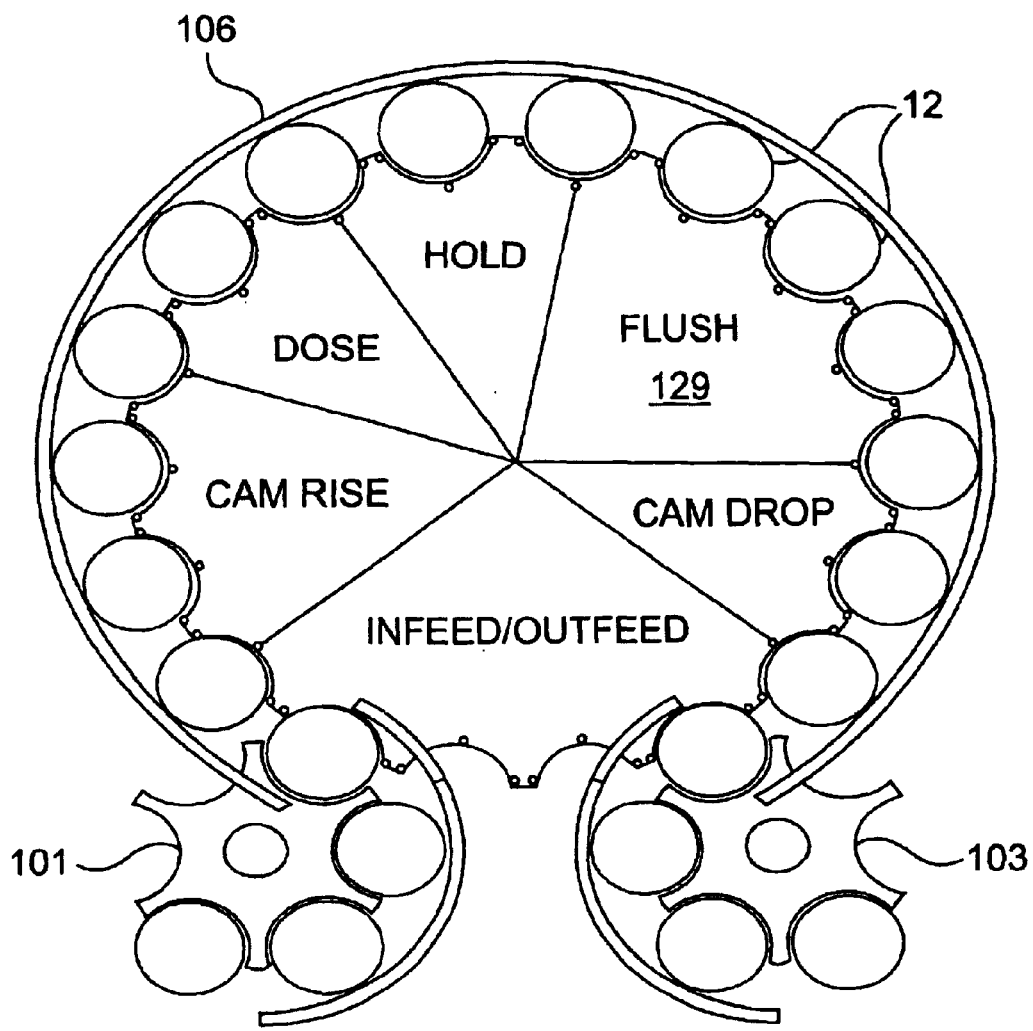
FIG. 7 is a plan view of the sterilization/sanitization apparatus of the present invention.

The sterilization/sanitation system 10 of the present invention is most effectively and efficiently utilized in an apparatus 100 for mass sterilizing or sanitizing the containers. This sterilization/sanitization apparatus 100 is shown in more detail in FIGS. 6 and 7. In order to most efficiently convey and sterilize or sanitize the containers, the apparatus is preferably of a carousel design. With this arrangement, the containers to be sterilized or sanitized are constantly moving throughout the various steps in the process to maximize the number of containers that can be processed in a given time period.

Based on the three mathematical relationships described above, the time required to sterilize or sanitize containers and subsequently remove residual peroxide can be determined and the size requirement for the carousel design can be determined. For example, given processing speed requirements of 625 10- to 20-ounce bottles per minute (bpm), 550 1-liter bpm or 300 2-liter bpm, the diameter of the sterilization/sanitization apparatus can range from 8.5–25.7 feet. Based on the large number of containers that can be processed per unit time, the area required for accommodating such an apparatus is relatively small. If need be, dosing could be effected on one carousel and elimination of residual could be effected on a second carousel, with the two carousels together occupying only slightly more floor space than would a single carousel that accomplished both tasks.

In apparatus 100, the previously-described sterilant supply section 20, flush gas supply section 30 and controller 60 can be incorporated in a unitary housing 102. Housing 102 includes the fluid connections 24, 33 and electrical connections 109 communicating with a carousel 106. Carousel 106 includes a base 108, as well as guide section 120, drive section 130 and gas delivery section 140. Guide section 120, drive section 130 and gas delivery section 140 are all housed within dose chamber or enclosure 114 (or a class 100 clean room) to contain the sterilant vapors within the apparatus and exclude airborne microbiological contaminants.

Because in the preferred embodiment the sterilant vapor is applied to the exteriors of the containers 12 as well as their interiors, apparatus 100 is designed to cause relative movement between containers 12 and corresponding delivery nozzles 50. In the preferred embodiment, the delivery nozzles 50 are not moved in the vertical direction, but rather containers 12 are raised and lowered relative to the nozzles. Alternatively, the nozzle assembly can be adapted to be lowered into the containers, which do not change their plane of rotation during the sterilization cycle. Further, the bottles can be raised to an intermediate position as the nozzle assembly is simultaneously lowered toward the intermediate position. To accomplish the embodiment wherein the nozzles are stationary, containers 12 are positioned on platforms 121, each connected at its lower end to a lifting rod 122. Each lifting rod 122 includes a follower roller 123 that follows a lift cam 124. Lift cam 124 has such a shape as to cause each lifting rod to rise from an in-feed zone up toward a sterilization and flush zone and then lower to an out-feed zone. Each lift rod 122 is connected to a drive wheel 125 by a bushing 126. Lift rods 122 are free to move relative to bushings 126 in the vertical direction. As drive wheel 125 rotates, guide rods 125 follow in a rotational direction to cause follow rollers 123 to ride along lift cam 124.

Lift rods 122 can be biased by unshown springs to a normally-raised position or to a normally-lowered position. Alternatively, lift rods 122 can be biased to be normally lowered by gravity. In any arrangement, containers 12 resting on platform 121 rise and fall with the path of the lift cam 124 as they rotate about the apparatus.

Drive wheel 125 is connected to a rotatable turret 127 that is journaled to base 108. Guides 128 and 129 are also connected to turret 127 and include surfaces for guiding and stabilizing the containers in circular and vertical movements. Turret 127 is driven by drive system 130. A motor 132 transmits motive force through transmission 131 that engages a gear 133 provided on the periphery of the turret. Motor 132 can be controlled by controller 60 provided in housing 102.

Gas delivery section 140 includes a gas distribution manifold 141, which is connected to the top of turret 127 and rotates with the turret. Sterilant supply line 24 and flush gas supply line 33 are connected to gas distribution manifold 141 by manifold supply lines 142 that are disposed within the hollow interior of turret 127. Manifold supply lines 142 are preferably stationary, but can communicate with gas distribution manifold 141 by ports communicating with arcuate slots, for example, such as is shown and described in U.S. Pat. No. 2,824,344. A number of exit lines 143 are connected to manifold body 142 to supply sterilant vapor or flush gas to valves 40. The number of exit lines 143 corresponds to the number of valves 40 designed in the apparatus. Valves 40 can be controlled mechanically by action of unshown cams or can be controlled by controller 60 with signals sent via electrical connections 104.

In operation, containers 12 enter apparatus 100 by being conveyed to in-feed turnstile 101 and, after processing, exit the apparatus through out-feed turnstile 103. Containers 12 are initially fed from in-feed turnstile 101 onto one of the platforms 121, with turret 127 continuously rotating. In the first stage after in-feeding, the container rises, due to the ramping action of the cam and follower roller, toward one of the delivery nozzles 50. Guides 128 and 129 include guide surfaces for each container to align the container with its corresponding delivery nozzle. In the preferred embodiment, each nozzle 50 discharges sterilant before it enters the opening of the container so as to spray sterilant around the upper exterior of the container.

The container is then further raised so that nozzle 50 enters the opening and is positioned within the container. Preferably, at its deepest extent, the end of nozzle 50 is disposed no closer than 15 millimeters from the bottom surface of the container and no closer than ⅙ the height of the container from the bottom surface. The sterilant continues to be discharged through the nozzle and the container enters a hold stage or zone.

After a predetermined holding period, which begins upon cessation of delivery of sterilant, the container enters the flush zone where valve 40 opens to discharge flush gas into the container. After the flushing process ends, container 12 is lowered and enters out-feed turnstile 103 to be discharged from the apparatus.

While the present invention has been described as to what is currently considered to be the preferred embodiments, it is to be understood that the invention is not limited to these embodiments. To the contrary, the invention is intended to cover various modifications and equivalent arrangements within the spirit and scope of the appended claims. The scope of the following claims is to be accorded the broadest interpretation so as to encompass all such modifications and equivalent structures and functions.

What is claimed is:

1. A method of sterilizing and/or sanitizing a container, said method comprising the steps of:

generating a sterilant vapor, the sterilant being maintained in a vapor state;

positioning a nozzle through an opening in the container and to a position in a range from just below a shoulder of the container to no closer than 15 mm from any internal surface of the container that is perpendicular to a principal direction of flow of sterilant vapor from the nozzle;

discharging the generated sterilant vapor through the nozzle and into the container; and purging the container of the discharged sterilant with gas from the nozzle.

2. A method according to claim 1, wherein after said positioning step, the nozzle is positioned no closer than 15 mm from the bottom of the container.

3. A method according to claim 1, wherein after said positioning step, the nozzle is inserted within ⅙ and ⅚ the height of the container.

4. A method according to claim 1, wherein the sterilant comprises hydrogen peroxide.

5. A method according to claim 1, further comprising the step of heating the nozzle.

6. A method according to claim 1, wherein the container is formed at least in part of PET.

7. A method according to claim 1, wherein said purging step comprises forcing heated gas into the container through the nozzle.

8. A method according to claim 1, wherein the nozzle has a diameter no greater than one-half the diameter of the opening of the container.

9. A method according to claim 1, wherein the sterilant vapor used in said discharging step and a gas used in said purging step are at temperatures no greater than 160° F.

10. A method according to claim 1, wherein said purging step is effected no longer than 30 seconds from said discharging step.

11. A method according to claim 1, further comprising the step of positioning the nozzle above the opening of the container and discharging the sterilant vapor onto the exterior of the container.

12. A method of sterilizing and/or sanitizing a container, the container having an opening of a predetermined diameter, a ratio of the interior surface area of the container to the cross-sectional area of the opening being at least 7.5, said method comprising the steps of:
   generating a sterilant vapor, the sterilant being maintained in a vapor state;
   positioning a nozzle through the opening in the container, the nozzle having a diameter no greater than one-half the predetermined diameter of the opening of the container, to a position in a range from just below a shoulder of the container to no closer than 15 mm from any internal surface of the container that is perpendicular to a principal direction of flow of sterilant vapor from the nozzle;
   discharging the generated sterilant vapor through the nozzle and into the container; and
   purging the container of the discharged sterilant with gas from the nozzle.

13. A method according to claim 12, wherein the sterilant comprises hydrogen peroxide.

14. A method according to claim 12, further comprising the step of heating the nozzle.

15. A method according to claim 12, wherein the container is formed at least in part of PET.

16. A method according to claim 12, wherein said purging step comprises forcing heated gas into the container through the nozzle.

17. A method according to claim 12, wherein after said positioning step the nozzle is inserted within ⅙ and ⅚ the height of the container.

18. A method according to claim 12, wherein the sterilant vapor used in said discharging step and a gas used in said purging step are at temperatures no greater than 160° F.

19. A method according to claim 12, wherein said purging step is effected no longer than 30 seconds from said discharging step.

20. A method according to claim 12, further comprising the step of positioning the nozzle above the opening of the container and discharging the sterilant vapor onto the exterior of the container.

21. A method according to claim 12, wherein the predetermined diameter of the opening of the container is no more than one-half the maximum diameter of the container.

22. A method of sterilizing and/or sanitizing a PET container, said method comprising the steps of:
   generating a sterilant vapor having a temperature no greater than 160° F., the sterilant being maintained in a vapor state;
   positioning a nozzle through an opening in the container;
   discharging the generated sterilant vapor through the nozzle and into the container; and
   purging the container of the discharged sterilant with a heated gas from the nozzle and having a temperature no greater than 160° F., wherein said purging step is completed no longer than 30 seconds from a beginning of said discharging step.

23. A method according to claim 22, wherein the sterilant comprises hydrogen peroxide.

24. A method according to claim 22, further comprising the step of heating the nozzle.

25. A method according to claim 22, wherein the container is formed in part of PET.

26. A method according to claim 22, wherein in said positioning step, the nozzle is disposed no closer than 15 mm from any internal surface of the container that is perpendicular to the direction of flow from the nozzle.

27. A method according to claim 22, wherein after said positioning step the nozzle is inserted within ⅙ and ⅚ the height of the container.

28. A method according to claim 22, wherein the opening of the container has a predetermined diameter, a ratio of the interior surface area of the container to the cross-sectional area of the opening is at least 7.5, and the nozzle has a diameter no greater than one-half the predetermined diameter of the opening of the container.

29. A method according to claim 22, further comprising the step of positioning the nozzle above the opening of the container and discharging the sterilant vapor onto the exterior of the container.

30. In combination, a container and an apparatus for sterilizing and/or sanitizing the container, said apparatus comprising:
   a generator of sterilant vapor, the sterilant being maintained in a vapor state;
   a nozzle communicating with said generator;
   a positioning mechanism for positioning said nozzle through an opening in the container and to a position in a range from just below a shoulder of the container to no closer than 15 mm from any internal surface of the container that is perpendicular to the direction of flow of sterilant vapor from the nozzle; and
   a controller for controlling discharging of the generated sterilant vapor through said nozzle and into the container and purging of the container of the discharged sterilant with gas from said nozzle.

31. A combination according to claim 30, wherein said positioning mechanism positions the nozzle no closer than 15 mm from the bottom of the container.

32. A combination according to claim 30, wherein said positioning mechanism inserts the nozzle within ⅙ and ⅚ the height of the container.

33. A combination according to claim 30, wherein the sterilant comprises hydrogen peroxide.

34. A combination according to claim 30, further comprising a heater for heating said nozzle.

35. A combination according to claim 30, wherein the container is formed at least in part of PET.

36. A combination according to claim 30, wherein in purging, said controller controls forcing of heated gas into the container through said nozzle.

37. A combination according to claim 30, wherein the opening of the container has a predetermined diameter, a ratio of the interior surface area of the container to the cross-sectional area of the opening is at least 7.5, and said nozzle has a diameter no greater than one-half the diameter of the opening of the container.

38. A combination according to claim 30, wherein said controller controls the sterilant vapor and a purge gas to be at temperatures no greater than 160° F.

39. A combination according to claim 30, wherein said controller controls purging to be effected no longer than 30 seconds from discharging of the sterilant.

40. A combination according to claim 30, wherein said controller further controls positioning of the nozzle above the opening of the container and discharging of the sterilant vapor onto the exterior of the container.

41. In combination, a container and an apparatus for sterilizing and/or sanitizing the container, the container having an opening of a predetermined diameter, a ratio of the interior surface area of the container to the cross-sectional area of the opening being at least 7.5, said apparatus comprising:

a generator of sterilant vapor, the sterilant being maintained in a vapor state;

a nozzle communicating with said generator, said nozzle having a diameter no greater than one-half the predetermined diameter of the opening of the container, to a position in a range from just below a shoulder of the container to no closer than 15 mm from any internal surface of the container that is perpendicular to a principal direction of flow of sterilant vapor from said nozzle;

a positioning mechanism for positioning said nozzle through the opening in the container; and a controller for controlling discharging of the generated sterilant vapor through said nozzle and into the container and purging of the container of the discharged sterilant with gas from said nozzle.

42. A combination according to claim 41, wherein the sterilant comprises hydrogen peroxide.

43. A combination according to claim 41, further comprising a heater for heating said nozzle.

44. A combination according to claim 41, wherein the container is formed at least in part of PET.

45. A combination according to claim 41, wherein in purging, said controller controls forcing of heated gas into the container through said nozzle.

46. A combination according to claim 41, wherein said positioning mechanism inserts the nozzle within ⅙ and ⅚ of the height of the container.

47. A combination according to claim 41, wherein said controller controls the sterilant vapor and a flush gas to be at temperatures no greater than 160° F.

48. A combination according to claim 41, wherein said controller controls purging to be effected no longer than 30 seconds from discharging of the sterilant.

49. A combination according to claim 41, wherein said controller further controls positioning of the nozzle above the opening of the container and discharging of the sterilant vapor onto the exterior of the container.

50. A combination according to claim 41, wherein the predetermined diameter of the opening of the container is no more than one-half the maximum diameter of the container.

51. In combination, a PET container and an apparatus for sterilizing and/or sanitizing the PET container, said apparatus comprising:

a generator of sterilant vapor having a temperature no greater than 160° F., the sterilant being maintained in a vapor state;

a nozzle communicating with said generator;

a positioning mechanism for positioning said nozzle through an opening in the container; and a controller for controlling discharging of the generated sterilant vapor through said nozzle and into the container and purging of the container of the discharged sterilant with a heated gas from said nozzle and having a temperature no greater than 160° F., wherein said controller controls purging to be completed no longer than 30 seconds from discharging of the sterilant.

52. A combination according to claim 51, wherein the sterilant comprises hydrogen peroxide.

53. A combination according to claim 51, further comprising a heater for heating said nozzle.

54. A combination according to claim 51, wherein the container is formed at least in part of PET.

55. A combination according to claim 51, wherein said positioning mechanism positions said nozzle to a position no closer than 15 mm from any internal surface of the container that is perpendicular to a principle direction of flow of sterilant vapor from the nozzle.

56. A combination according to claim 51, wherein said positioning mechanism inserts the nozzle within ⅙ and ⅚ the height of the container.

57. A combination according to claim 51, wherein the opening of the container has a predetermined diameter, a ratio of the interior surface area of the container to the cross-sectional area of the opening is at least 7.5, and said nozzle has a diameter no greater than one-half the diameter of the opening of the container.

58. A combination according to claim 51, wherein said controller further controls positioning of the nozzle above the opening of the container and discharging of the sterilant vapor onto the exterior of the container.

59. A method of sterilizing and/or sanitizing a container having a volume b (1), said method comprising the steps of:

generating hydrogen peroxide sterilant vapor having a temperature $T_1$ (° F.), the sterilant being maintained in a vapor state;

discharging a mass a (mg) of the generated sterilant vapor into the container; and purging the container of the discharged sterilant with heated gas having a volume c (1) and a temperature $T_2$ (° F.), wherein said generating, discharging and purging steps are controlled so as to effect a reduction of Bacillus spores in the container by a predetermined amount X (log) by satisfying the following equation $$X=(0.138 \times a/b)+(0.066 \times T_1)-(0.00083 \times c/b)+(0.021 \times T_2)+(0.008347 \times d)-11.357,$$

wherein d is the ambient relative humidity (% RH).

60. A method according to claim 59, wherein the spores are *Bacillus subtilis* var. *globigii*.

61. A method according to claim 59, wherein the predetermined reduction amount (X) of the spores in the container equals at least 6 log.

62. A method according to claim 59, wherein the residual sterilant is reduced in said purging step to a desired level (Z) (mg/l) by satisfying the following equation:

$$Z=(0.030 \times a/b)-(0.043 \times T_1)-(0.040 \times c/b)-(0.075 \times T_2)+15.747.$$

63. A method according to claim 59, wherein the sterilant comprises 35% hydrogen peroxide.

64. A method of sterilizing and/or sanitizing a container having a volume b (1), said method comprising the steps of:

generating a hydrogen peroxide sterilant vapor having a temperature $T_1$ (° F.), the sterilant being maintained in a vapor state;

discharging a mass a (mg) of the generated sterilant vapor into the container; and purging the container of the discharged sterilant with heated gas having a volume c (1) and a temperature $T_2$ (° F.), wherein said generating, discharging and purging steps are controlled so as to effect a reduction of yeast ascospores in the container by a predetermined amount Y (log) by satisfying the following equation $$Y=(0.063 \times a/b)+(0.023 \times T_1)-(0.00036 \times c/b)+(0.052 \times T_2)+(0.009 \times d)-3.611,$$

wherein d is the ambient relative humidity (% RH).

65. A method according to claim 64, wherein the ascospores are of the yeast *Saccharomyces cerevisiae*.

66. A method according to claim 64, wherein the predetermined reduction amount (Y) of the ascospores in the container equals at least 5 log.

67. A method according to claim 64, wherein the residual sterilant is reduced in said purging step to a desired level (mg/l) (Z) by satisfying the following equation:

$$Z = (0.030 \times a/b) - (0.043 \times T_1) - (0.040 \times c/b) - (0.075 \times T_2) + 15.74.$$

68. A method according to claim 64, wherein the sterilant comprises 35% hydrogen peroxide.

69. A method of sterilizing and/or sanitizing a non-heat-set PET container having a volume b (l), said method comprising the steps of:

generating hydrogen peroxide sterilant vapor having a temperature $T_1$(° F.), the sterilant being maintained in a vapor state;

discharging a mass a (mg) of the generated sterilant vapor into the container; and purging the container of the discharged sterilant with heated gas having a volume c (l) and a temperature $T_2$ (° F.), wherein said generating, discharging and purging steps are controlled so as to effect a reduction of the sterilant in the container to a predetermined amount Z (mg/l) at 24 hours after said purging step by satisfying the following equation $$Z = (0.030 \times a/b) - (0.043 \times T_1) - (0.040 \times c/b) - (0.075 \times T_2) + 15.747.$$

70. A method according to claim 69, wherein the sterilant comprises 35% hydrogen peroxide.

71. A method according to claim 69, wherein the predetermined amount is 0.5 mg/l at 24 hours after said purging step.

* * * * *